United States Patent
Sarker et al.

(10) Patent No.: US 9,622,479 B2
(45) Date of Patent: Apr. 18, 2017

(54) BORON COMPLEXES WITH GRADUAL 1-METHYLCYCLOPROPENE RELEASING CAPABILITY

(71) Applicant: The United States of America, as represented by the Secretary of Agriculture, Washington, DC (US)

(72) Inventors: Majher I. Sarker, Philadelphia, PA (US); Lin S. Liu, Blue Bell, PA (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 14/749,122

(22) Filed: Jun. 24, 2015

(65) Prior Publication Data

US 2015/0366212 A1    Dec. 24, 2015

Related U.S. Application Data

(60) Provisional application No. 62/017,535, filed on Jun. 26, 2014, provisional application No. 62/016,317, filed on Jun. 24, 2014.

(51) Int. Cl.
| | |
|---|---|
| A01N 55/08 | (2006.01) |
| A01N 59/14 | (2006.01) |
| A61K 33/22 | (2006.01) |
| C07F 5/02 | (2006.01) |
| A01N 3/02 | (2006.01) |
| C07F 7/22 | (2006.01) |

(52) U.S. Cl.
CPC ............. *A01N 55/08* (2013.01); *A01N 3/02* (2013.01); *C07F 5/027* (2013.01); *C07F 7/2212* (2013.01)

(58) Field of Classification Search
None
See application file for complete search history.

(56) References Cited

PUBLICATIONS

Bubnov et al., Dibutyl(methylenecyclopropyl)borane, Izvestiya Akademii Nauk SSSR, Seriya Khimicheskaya, 1988, 9, 2184) ABS.*

* cited by examiner

*Primary Examiner* — Alton Pryor
(74) *Attorney, Agent, or Firm* — G. Byron Stover; John D. Fado

(57) ABSTRACT

Compounds having one of the following formulae:

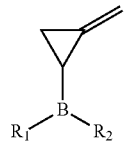

wherein $R^1$ and $R^2$ are alkyl or aryl and $R^1$ and $R^2$ may be the same or different,

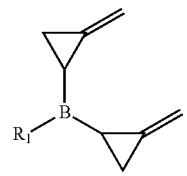

wherein $R^1$ is alkyl or aryl, or

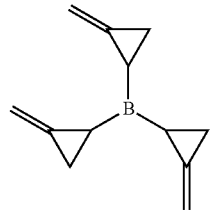

wherein alkyl is a linear or branched, saturated or unsaturated alkyl having C1-20 and wherein aryl is an aromatic ring having C1-15. Also methods of using the compounds, including method of inhibiting an ethylene response in a plant.

11 Claims, 16 Drawing Sheets
(6 of 16 Drawing Sheet(s) Filed in Color)

BORON COMPLEXES WITH GRADUAL 1-METHYLCYCLOPROPENE RELEASING CAPABILITY

REFERENCE TO RELATED APPLICATION

This application claims the benefit of U.S. Provisional application Ser. No. 62/017535, filed 26 Jun. 2014, and 62/016,317, filed 8 Oct. 2014, which are incorporated herein by reference in their entirety.

BACKGROUND OF THE INVENTION

Compounds having one of the following formulae are disclosed:

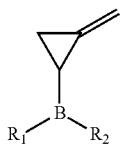

wherein $R^1$ and $R^2$ are alkyl or aryl and $R^1$ and $R^2$ may be the same or different,

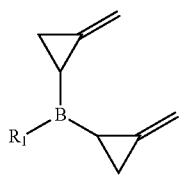

wherein $R^1$ is alkyl or aryl, or

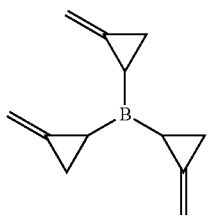

wherein alkyl is a linear or branched, saturated or unsaturated alkyl having C1-20 and wherein aryl is an aromatic ring having C6-15. Also methods of using the compounds, including methods of inhibiting an ethylene response in a plant.

1-Methylcyclopropene (1-MCP) is a cyclopropene derivative used as a synthetic plant growth regulator. It is structurally related to the natural plant hormone ethylene and is being used commercially to keep fruits, flowers or vegetables fresh, either by preventing or delaying the natural ripening process. It is also used to prevent premature wilting, leaf yellowing, premature opening of flowers as well as premature death (Chow, B., and P. McCourt, Genes Dev., 20 (15): 1998-2008 (2006); De Paepe, A., and D. Van der Straeten, Vitam, Horm., 72: 399-430 (2005)).

Ethylene is a plant hormone that exists as a gas and acts at trace levels throughout the life of a plant by stimulating or regulating various processes. There are three groups of compounds which bind to plant receptors. The first group that includes ethylene, carbon monoxide, acetylene or iso-cyanides, binds to the receptors and induce an ethylene response, such as the ripening of climacteric fruit, the opening of flowers and the shedding of leaves (Chow and McCourt 2006, DePaepe and Van der Straeten 2005). The second group containing olefins are weakly binding compounds that compete with ethylene for a receptor binding site and prevent it from inducing an ethylene response. They can only work if the ethylene level is relatively low. At high levels of ethylene, an ethylene response would still be observed because it will overrule the action of the inhibitor. The third group of compounds also interacts with the receptors and competes with ethylene for binding. However, in this case a single exposure of plant tissue to these compounds is enough to prevent ethylene from binding even at a very high level of ethylene, although this action disappears after several days either due to the diffusion of the compounds from the binding sites or the development of new receptors. 1-MCP is an important member of the third group. The tight binding characteristic of 1-MCP to the ethylene receptor in plants blocks the activities of ethylene (Serek, M., et al., Physiol. Plant.,94 (2): 229-232 (1995); Sisler, E. C., and M. Serek, Plant Biol., 5 (5): 473-480 (2003)).

Nationally, we dump $43 billion worth of food every year, most of which is composed of rotting fruits and vegetables. So it is of great importance to explore keeping fruits and vegetables fresh for a longer period of time. Cyclodextrin is being used as an encapsulating agent for 1-MCP to facilitate handling but it does not allow a controlled release of 1-MCP. Therefore, it can only be used in enclosed sites, such as coolers, truck trailers, greenhouses, storage facilities and shipping containers.

Thus there is a need for new compounds which will keep fruits and vegetables fresh for a longer period of time. Also needed are new compounds to be used in crop fields for the protection of crop yield from extreme weather conditions.

SUMMARY OF THE INVENTION

Compounds having one of the following formulae are disclosed:

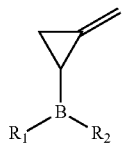

wherein $R^1$ and $R^2$ are alkyl or aryl and $R^1$ and $R^2$ may be the same or different,

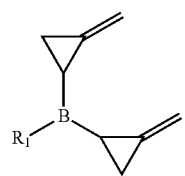

wherein $R^1$ is alkyl or aryl, or

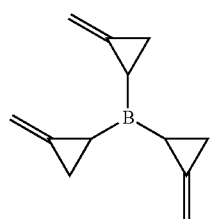

wherein alkyl is a linear or branched, saturated or unsaturated alkyl having C1-20 and wherein aryl is an aromatic ring having C6-15. Also methods of using the compounds, including methods of inhibiting an ethylene response in a plant, methods of inhibiting abscission in a plant, methods of prolonging the life of a cut flower.

This summary is provided to introduce a selection of concepts in a simplified form that are further described below in the detailed description. This summary is not intended to identify key features or essential features of the claimed subject matter, nor is it intended as an aid in determining the scope of the claimed subject matter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
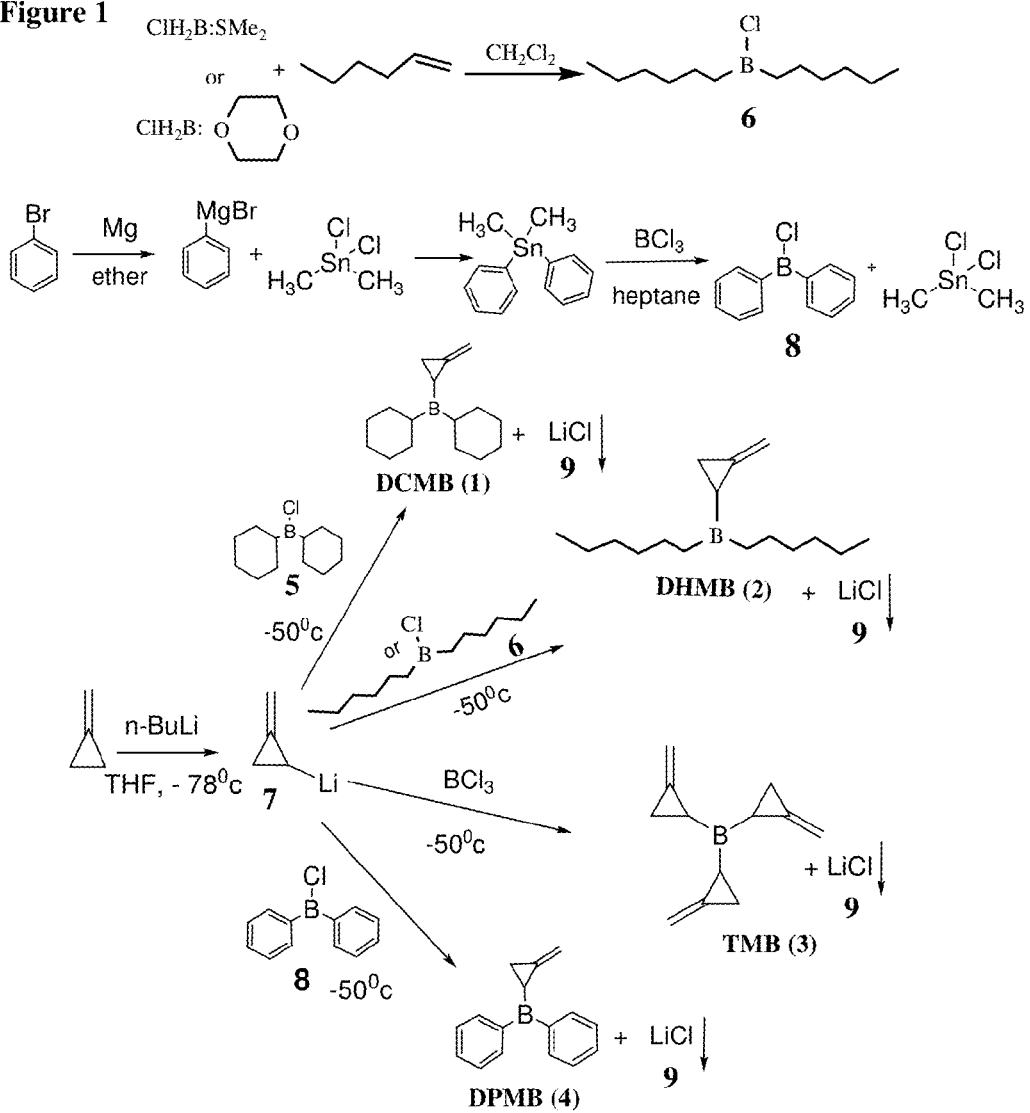
FIG. 1 shows a general scheme for preparing compound 1-4 as described below.
Figure 2:
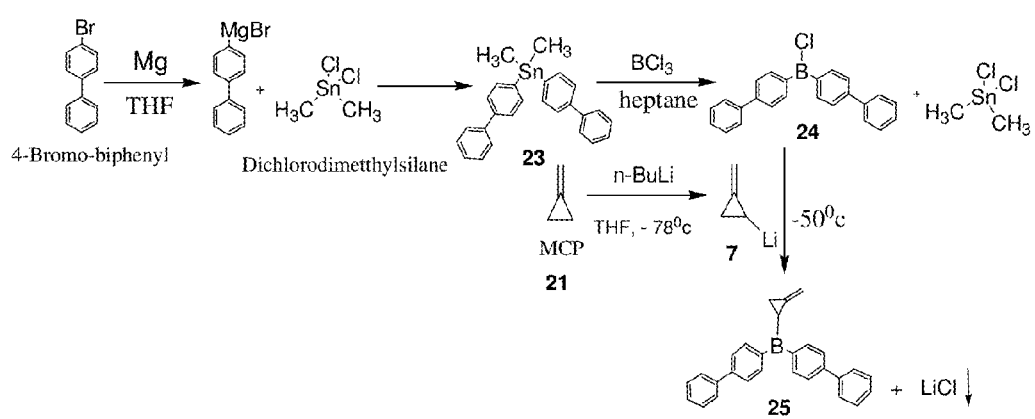
FIG. 2 shows a general scheme for preparing compound Bis-biphenyl-4-yl-(2-methylene-cyclopropyl)-borane, BPMB (25) as described below.
Figure 3:
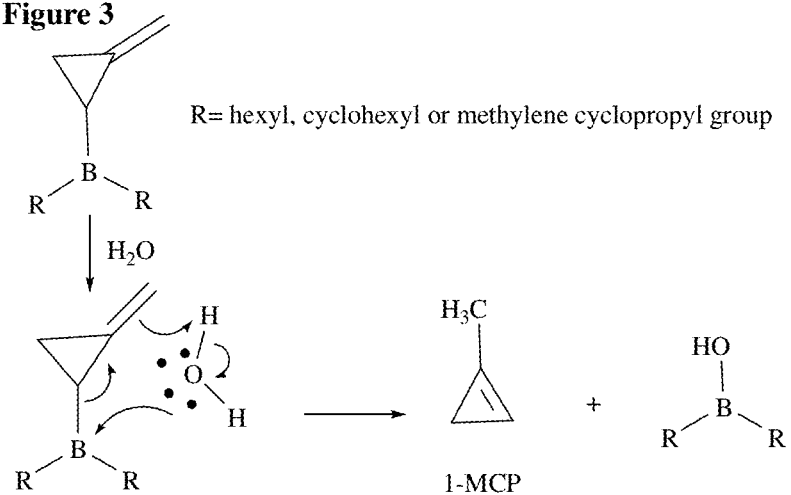
FIG. 3 shows a general scheme for the release of MCP from the boron compounds described below.

Compounds having one of the following formulae are disclosed:

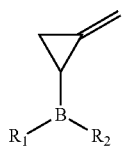

wherein $R^1$ and $R^2$ are alkyl or aryl and $R^1$ and $R^2$ may be the same or different,

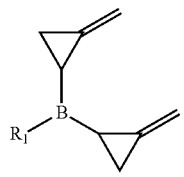

wherein $R^1$ is alkyl or aryl, or

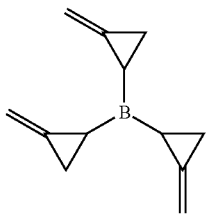

wherein alkyl is a linear or branched, saturated or unsaturated alkyl having C1-20 and wherein aryl is an aromatic ring having C6-15. Also methods of using the compounds, including methods of inhibiting an ethylene response in a plant.

Due to the low boiling point of 1-MCP (~12° C.), it is a gas at room temperature which creates difficulties in its handling and controlled release. To overcome these difficulties, we have synthesized boron derivatives of methylene cyclopropane (MCP) that have high boiling points and the capability of gradual release of 1-MCP under ambient conditions. Examples of these boron derivatives include compounds 1, 2, and 3 described herein. The boron complexes described herein provide both better handling capability and sustained release of 1-MCP. It is evident from our investigations that boron complexes have the potential to release 1-MCP in a controlled way which not only solves the existing problems but also will lead to development of new complexes which can be used directly in fields to protect crops from moderate heat and drought conditions and potentially prevent millions of dollars in crop losses around the globe especially in hot atmosphere. The compounds disclosed herein can also be used in crop fields for the protection of crop yield from extreme weather.

Boron derivatives of methylene cyclopropane have the formulae:

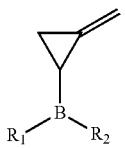

wherein $R^1$ and $R^2$ are alkyl or aryl ($R^1$ and $R^2$ may be the same or different; neither can be H)

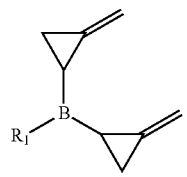

wherein $R^1$ is alkyl or aryl ($R^1$ cannot be H), or

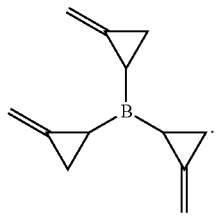

The term "alkyl" as used herein refers to linear or branched, saturated or unsaturated alkyls. Examples include, but are not limited to, methyl, ethyl, propyl, isopropyl, and butyl. Alkyl groups of the present invention are preferably linear and saturated. Generally C1-20, preferably C4-20, more preferably C5-18, more preferably C6-16. Examples also include (2-Methyl-butyl)-bis-(2-methylene-cyclopropyl)-borane (branched), Hex-1-enyl-bis-(2-methylene-cyclopropyl)-borane (unsaturated), Bis-(2-methylene-cyclopropyl)-oct-1-enyl-borane (unsaturated), [2-(4-Methyl-cyclohex-3-enyl)-propyl]-bis-(2-methylene-cyclopropyl)-borane. The term "aryl" as used herein refers to any functional-group or substituent derived from an aromatic ring (e.g., phenyl). Generally C6-15, preferably C6-14, more preferably C6-12. For example, (2-methylene-cyclopropyl)-diphenyl-borane and bis-biphenyl-4-yl-(2-methylene-cyclopropyl)-borane. Examples also include (2-Methylene-cyclopropyl)-di-naphthalen-1-yl-borane (26), (2-Methylene-cyclopropyl)-di-naphthalen-2-yl-borane (27), (2-Methylene-cyclopropyl)-di-phenanthren-9-yl-borane (28), DPMB (4) diphenyl-(2-methylene-cyclopropyl)-borane, bis-biphenyl-4-yl-(2-methylene-cyclopropyl)-borane, BPMB (25), bis-biphenyl-4-yl-dimethyl-stannane (23), bis-biphenyl-4-yl-chloro-borane (24), bis-2-methyl-naphthyl-1-yl-(2-methylene-cyclopropyl)-borane, bis-fluorenyl-3-yl-(2-methylene-cyclopropyl)-borane, bis-fluorenyl-9-yl-(2-methylene-cyclopropyl)-borane, bis-diphenylmethyl-(2-methylene-cyclopropyl)-borane, bis-anthracenyl-9-yl-(2-methylene-cyclopropyl)-borane.

The term "plant" is used in a generic sense herein, and encompasses woody-stemmed plants such as trees and shrubs. Plants to be treated by the methods described herein include whole plants and any portions thereof, such as field crops, potted plants, cut flowers (stems and flowers), and harvested fruits and vegetables.

Plants treated by the methods of the present invention are preferably treated with a non-phytotoxic amount of the active compound.

The compounds can be employed to combat numerous different ethylene responses. Ethylene responses may be initiated by either exogenous or endogenous sources of ethylene. Ethylene responses include, for example, the ripening and/or senescence of flowers, fruits and vegetables, abscission of foliage, flowers and fruit, the prolongation of the life of ornamentals such as potted plants, cut flowers, shrubbery, and dormant seedlings, in some plants (e.g., pea) the inhibition of growth, and in other plants (e.g., rice) the stimulation of growth.

Vegetables which may be treated by the methods to inhibit ripening and/or senescence include leafy green vegetables such as lettuce (e.g., *Lactuea sativa*), spinach (*Spinaca oleracea*), and cabbage (*Brassica oleracea*), various roots, such as potatoes (*Solanum tuberosum*) and carrots (*Daucus*), bulbs, such as onions (*Allium* sp.), herbs, such as basil (*Ocimum basilicum*), oregano (*Origanum vulgare*), dill (*Anethum graveolens*), as well as soybean (*Glycine max*), lima beans (*Phaseolus limensis*), peas (*Lathyrus* spp.), corn (*Zea mays*), broccoli (*Brassica oleracea italica*), cauliflower (*Brassica oleracea botrytis*), and asparagus (*Asparagus officinalis*).

Fruits which may be treated by the methods of the present invention to inhibit ripening include tomatoes (*Lycopersicon esculentum; Solarium lycopersicum*), apples (*Malus domestica*), bananas (*Musa sapientum*), pears (*Pyrus communis*), papaya (*Carica papaya*), mangoes (*Mangifera indica*), peaches (*Prunus persica*) apricots (*Prunus armeniaca*), nectarines (*Prunus persica nectarina*), oranges (*Citrus* sp.), lemons (Citrus limonia), lines (Citrus aurantyblia), grapefruit (*Citrus paradisi*), tangerines (*Citrus nobilis deliciosa*), kiwi (*Actinidia chinenus*), melons such as cantaloupe (*Cucumis cantalupensis*) and musk melon (*C. melo*), pineapple (*Aranas comosus*), persimmon (*Diospyros* sp.), various small fruits including berries such as strawberries (*Fragaria*), blueberries (*Vaccinium* sp.) and raspberries (e.g., *Rubus ursinus*), green beans (*Phaseolus vulgaris*), members of the genus *Cucumis* such as cucumber (*C. sativus*), and avocados (*Persea americana*).

Ornamental plants which may be treated by the methods to inhibit senescence and/or to prolong flower life and appearance (e.g., delay wilting), include potted ornamentals, and cut flowers. Potted ornamentals and cut flowers which may be treated include azalea (*Rhododendron* spp.), hydrangea (*Macrophylla hydrangea*) hybiscus (*Hibiscus rosa-sanensis*), snapdragons (*Antirrhinum* sp.), poinsettia (*Euphorbia pulcherima*), cactus (e.g. *Cactaceae schlumbergera truncata*), begonias (*Begonia* sp.), roses (*Rosa* spp.), tulips (*Tulipa* sp.), daffodils (*Narcissus* spp.), petunias (*Petunia hybrida*), carnation (*Dianthus caryophyllus*), lily (e.g., *Lilium* sp.), gladiolus (*Gladiolus* sp.), alstroemeria (*Alstoemeria brasiliensis*), anemone (e.g., *Anemone blanda*), columbine (*Aquilegia* sp.), aralia (e.g., *Aralia chinensis*), aster (e.g., *Aster carolinianus*), bougainvillea (*Bougainvillea* sp.), camellia (*Camellia* sp.), bellflower (*Campanula* sp.), cockscomb (*Celosia* sp.), falsecypress (*Chamaecyparis* sp.), chrysanthemum (*Chrysanthemum* sp.), clematis (*Clematis* sp.), cyclamen (*Cyclamen* sp.), freesia (e.g., *Freesia refracta*), and orchids of the family Orchidaceae.

Plants which may be treated by the methods to inhibit abscission of foliage, flowers and fruit include cotton (*Gossypium* spp.), apples, pears, cherries (*Prunus avium*), pecans (*Carva illinoensis*), grapes (*Vitis vinifera*), olives (e.g., *Vitis vinifera* and *Olea europaea*), coffee (*Coffea arabica*), snapbeans (*Phaseolus vulgaris*), and weeping fig (*Ficus benjamina*), as well as dormant seedlings such as various fruit trees including apple, ornamental plants, shrubbery, and tree seedlings. In addition, shrubbery which may be treated to inhibit abscission of foliage include privet (*Ligustrum* sp.), photinea (*Photinia* sp.), holly (*Ilex* sp.) ferns of the family Polypodiaceae, schefflera (*Schefflera* sp.), aglaonema (*Aglaonema* sp.), cotoneaster (*Cotoneaster* sp.), barberry (*Berberis* sp.), waxmyrtle (*Myrica* sp,) abelia (*Abelia* sp.), acacia (*Acacia* sp.) and bromeliades of the family Bromeliaceae.

The active compounds can be applied to plants by any suitable means. They may be applied alone, or in combination with inert carriers. The active compound may be applied alone in gaseous, liquid, or solid form, by contacting the compound to the plant to be treated. Alternatively, the compound may be applied with an inert carrier. Suitable solid carriers include dust. The active compound may also be suspended in a liquid solution, as an organic solvent or an aqueous solution. Similarly, the gaseous form of the compound may be dispersed in an inert gaseous carrier to provide a gaseous solution.

Numerous organic solvents may be used as a carrier for the active compounds, e.g., hydrocarbons such as hexane, benzene, toluene, xylene, kerosene, diesel oil, fuel oil and petroleum naphtha, ketones such as acetone, methyl ethyl ketone and cyclohexanone, chlorinated hydrocarbons such as carbon tetrachloride, esters such as ethyl acetate, amyl acetate and butyl acetate, ethers, e.g., ethylene glycol monomethyl ether and diethylene glycol monomethyl ether, alcohols, e.g., ethanol, methanol, isopropanol, amyl alcohol, ethylene glycol, propylene glycol, butyl carbitol acetate and glycerine.

Mixtures of water and organic solvents, either as solutions or emulsions, can he also employed as carriers for the active compound.

The active compounds can also be applied with adjuvants or carriers such as talc, pyrophyllite, synthetic fine silica, attapulgus clay (attaclay), kieselguhr, chalk, diatomaceous earth, lime, calcium carbonate, bentonite, fuller's earth, cottonseed hulls, wheat flour, soybean flour pumice, tripoli, wood flour, walnut shell flour, redwood flour and lignin.

It may be desirable to incorporate a wetting agent in the compositions. Such wetting agents may be employed in both the solid and liquid compositions. The wetting agent can be anionic, cationic or nonionic in character.

Typical classes of wetting agents include alkyl sulfonate salts, alkylaryl sulfonate salts, alkyl sulfate salts, alkylamide sulfonate salts, alkylaryl polyether alcohols, fatty acid esters of polyhydric alcohols and the alkylene oxide addition products of such esters, and addition products of long chain mercaptans and alkylene oxides. Typical examples of such wetting agents include the sodium alkylbenzene suifonates having 10 to 18 carbon atoms in the alkyl group, alkylphenol ethylene oxide condensation products, e.g., p-isooctylphenol condensed with 10 ethylene oxide units, soaps, e.g., sodium stearate and potassium oleate, sodium salt of propylnaphthalene sulfonic acid (di-2-ethylhexyl), ester of sodium sulfosuccinic acid, sodium lauryl sulfate, sodium stearate and potassium oleate, sodium salt of the sulfonated monoglyccride of coconut fatty acids, sorbitan, sesquioleate, lauryl trimethyl ammonium chloride, octadecyl trimethyl ammonium chloride, polyethylene glycol lauryl ether, polyethylene esters of fatty acids and rosin acids, e.g., Ethofat 7 and 13, sodium N-methyl-N-oleylaurate, Turkey Red oil, sodium dibutylnaphthalene sulfonate, sodium lignin sulfonate (Marasperse N), polyethylene glycol stearate, sodium dodecylbeuzene sulfonate, tertiary dodecyl polyethylene glycol thioether (Nonionic 218), long chain ethylene oxide-propylene oxide condensation products, e.g., Pluronic 61 (molecular weight 1,000), sorbitan sesquioleate, polyethylene glycol ester of tall oil acids, sodium octyl phenoxyethoxyethyl sulfate, polyoxyethylene (20) sorbitan monolaurate ("Tween 20") tris (polyoxyethylene) sorbitan monostearate ("Tween 60"), and sodium dihexyl sulfosuccinate.

The solid, liquid, and gaseous formulations can be prepared by any of the conventional procedures. Thus, the active ingredient, in finely divided form if a solid, may be tumbled together with finely divided solid carrier. Alternatively, the active ingredient in liquid form, including solutions, dispersions, emulsions and suspensions thereof, may be admixed with the solid carrier in finely divided form.

Unless defined otherwise, all technical and scientific terms used herein have the same meaning as commonly understood by one of ordinary skill in the art to which the invention belongs. As used herein, the term "about" refers to a quantity, level, value or amount that varies by as much as 30%, preferably by as much as 20%, and more preferably by as much as 10% to a reference quantity, level, value or amount. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Boron complexes: It was desirable to preferentially study boron complexes of MCP (11) due to their high boiling point and moisture sensitivity. At this point we synthesized and investigated five boron complexes of MCP (compounds 1,2,3,4,. Dialkyl-(2-methylene-cyclopropyl)-borane (1 & 2) was been prepared by the reaction of dialkyl-chloroborane (5, 6) with lithiated MCP (7), whereas, tris-(2-methylene-cyclopropyl)-borane (3) was synthesized following the reaction between boron tri-chloride (10) and lithiated MCP (7). Dicyclohexyl-chloroborane (5) was purchased from Aldrich. Dihexyl-chloroborane (6) was prepared by the hydroboration reaction of 1-hexene and chloroborane methyl sulfide complex (Bolton, R., et al., Aust. J. Chem., 40: 987-989 (1987)) (11) or chloroborane, dioxane complex (12)(Kanth, J. V., and H. C. Brown, Org. Lett., 1(2): 315-317 (1999); Kanth, J. V., and H. C. Brown, J. Org Chem., 66: 5359-5365 (2001)), Chloroborane methyl sulfide complex was purchased from Aldrich and chloroborane dioxane complex was prepared following a two-step procedure (see below; Kanth and Brown 1999, Kanth and Brown 2001), Methylene cyclopropane (MCP) was prepared from the reaction between potassium-[bis(trimethylsilyl)]amide (13) and methallyl chloride (14) (Binger, P., et al., Synthesis, 10: 1344-1346 (2002)).

Preparation of chloroborane dioxane complex:

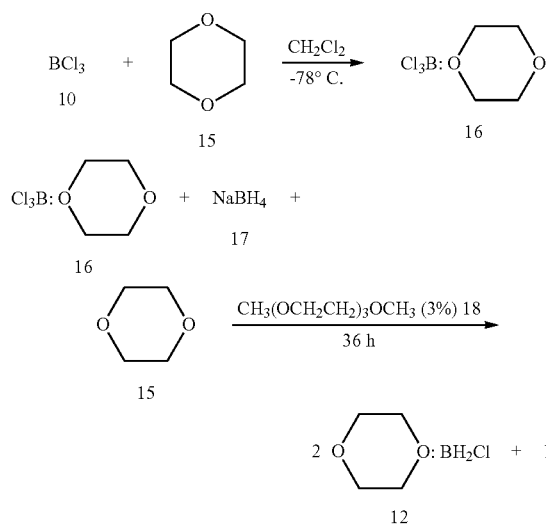

An oven-dried marked centrifuge tube provided with a septum inlet was cooled to −75° C. under argon. Boron trichloride gas (10) (14.2 g, 121.2 mmol) was condensed into the tube and transferred into an oven-dried 100 mL schlenk flask under argon. Dichloromethane (25 mL) was added and stirred for 10 min. To this solution dioxane (15) (10.7 g, 121 mmol) was added slowly during 30 min and the contents were slowly brought to 0° C. Evaporation of $CH_2Cl_2$ under vacuum provided a white solid of dioxane-$BCl_3$ (16). $^{11}B$ NMR (in $CH_2Cl_2$): +9.47 ppm (singlet).

The dioxane-$BCl_3$ (16) thus obtained was stable for several hours at 0° C. To this $BCl_3$ adduct (16) 32.0 g (363 mmol) of dioxane (15) was added at 10° C. under argon. The flask was charged with 13.7 g (363 mmol) of $NaBH_4$ (17) and stirred for 10 min. Triglyme (18) (4.5 mL, 25 mmol) was added to the reaction mixture and the contents were further stirred at room temperature for 36 h. The contents were allowed to settle by centrifuge and the clear supernatant solution decanted under argon. The adduct (12) thus obtained is 2.9 M in $BH_2Cl$. $^{11}B$ NMR: +6.8 ppm, triplet, 97%.

Preparation of alkyl-chloroborane with sulfide complex:

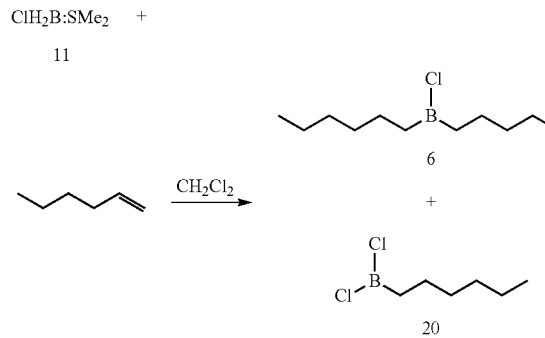

A clean oven-dried 100 mL schlenk flask was cooled in an ice bath and charged with 82 mL of anhydrous dichloromethane under argon. 1-hexene (12.8 mL, 100 mmol) was added and stirred for 10 min. $ClH_2B:SMe_2$ (5.8 mL, 50 mmol) was added slowly over 15 min. The final solution is 0.5M in $BH_2Cl$ and 1.0 M in 1-hexene. The reaction mixture was stirred for 2 h at room temperature. The solvent was then removed by using rotary evaporator. Vacuum distillation provided a mixture of dihexylchlorborane (6) (79% from $^{11}B$ NMR, 76 ppm) and hexyldichloroboron (20) (21% from $^{11}B$ NMR, 39 ppm).

Preparation of alkyl-chloroborane with dioxane complex:

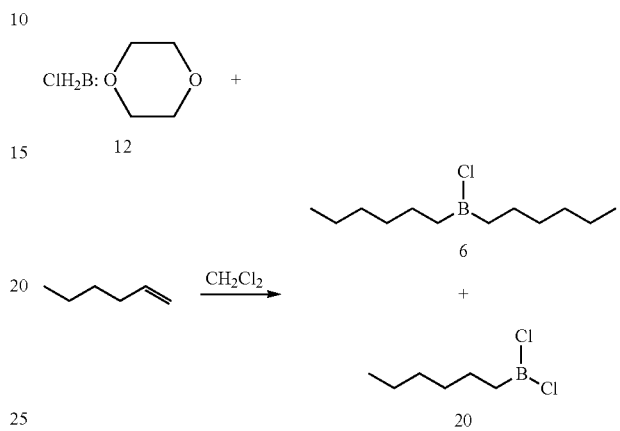

A clean oven-dried 100 mL schlenk flask was cooled in an ice bath and charged with 5 ml (14.5 mmol $BH_2Cl$) of $ClH_2B$:dioxane complex (12) and 20.4 mL of anhydrous dichloromethane under argon. The mixture was stirred for 10 min. 1-hexene (3.6 mL, 29 mmol) was added slowly over 15 min. The final solution is 0.5M in $BH_2Cl$ and 1.0 M in 1-hexene. The reaction mixture was stirred for 20 min at room temperature. The solvent was then removed under vacuum. Vacuum distillation provided a mixture of dihexylchlorborane (6) (80% from $^{11}B$ NMR: δ 75) and hexyldichloroboron (20) (20% from $^{11}B$ NMR: δ 39 ppm).

Preparation of MCP (methylene cyclopropane):

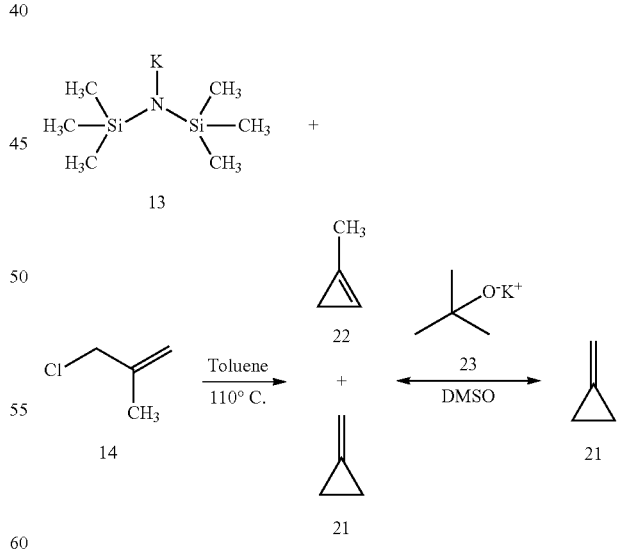

An oven-dried three neck flask equipped with a condenser charged with 10.5 g (50.1 mmol) of potassium[bis(trimethylsilyl)]amide (13) dissolved in 17 mL of toluene. The other end of the condenser was connected with an air-tight tube in a cold trap (−78° C.). The solution was boiled at 110° C. and 3.7 g (41.5 mmol) of methallyl chloride (14) was added slowly with a syringe over 15 min. The reflux was continued for another 30 min and a stream of argon was passed. 1.9 mL of the mixture of MCP (21) and 1-MCP (22) was collected in the cold trap. The mixture was bubbled into the solution of t-buOK (23) (0.31 g, 2.8 mmol) in 2 mL of DMSO at 60° C. and collected in a cold trap (−78° C.) to provide 0.96 g of MCP (21). $^1$H NMR (CDCl$_3$) δ 0.78-1.34 (m, 4H), 5.15-5.65 (m, 2H); $^{13}$C NMR (CDCl$_3$) δ 32.1, 103.2, 131.1.

Preparation of complex of dicyclohexyl-(2-methylene-cyclopropyl)-borane:

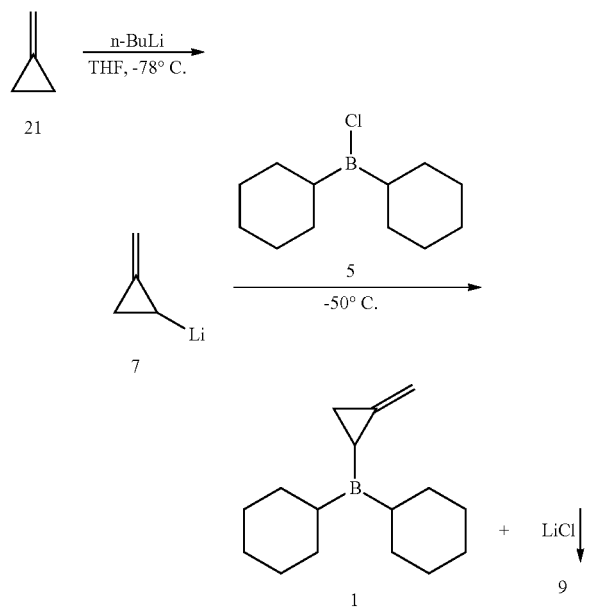

An oven-dried 100 mL, schlenk flask cooled at −78° C. was charged with MCP (21) (0.91 g, 16.9 mmol) in 30 mL, of anhydrous THF. 6.5 mL, of 2.5 M n-BuLi in hexane (16.2 mmol) was added slowly and stirred at room temperature for 3 h. The mixture was cooled at −50° C. and 3.4 g (16.0 mmol) of dicyclohexylchloroborane (5) was added slowly over 15 min. The reaction mixture was stirred at room temperature for 24 h. The solution was filtered to remove salt (9) and concentrated in vacuo. The precipitated solid is removed by filtration. The reaction mixture was dissolved in 30 mL of pentane and passed through a pad of celite under nitrogen. The solution was concentrated in vacuo and dried under vacuum to obtain the complex of dicyclohexyl-(2-methylene-cyclopropyl)-borane (1). $^{11}$B NMR (CDCl$_3$): δ 30.6.

Preparation of complex of dihexyl-(2-methylene-cyclopropyl)-borane: An oven-dried 100 mL schlenk flask cooled at −78° C. was charged with MCP (21) (1.09 g, 20.3 mmol) in 30 mL of anhydrous THF. 8 mL of 2.5 M n-BuLi in hexane (20 mmol) was added slowly and stirred at room temperature for 4 h. The mixture was cooled at −50° C. and 3.7 g (total 20 mmol) of the mixture of hexylchloroborane (6, 20) was added slowly over 15 min. The reaction mixture was stirred at room temperature for 36 h. The solution was filtered to remove salt and concentrated in vacuo. The precipitated solid was removed by filtration. The reaction mixture was dissolved in 50 mL of pentane and passed through a pad of alumina under nitrogen. The solution was concentrated in vacuo and dried under vacuum to obtain dihexyl-(2-methylene-cyclopropyl)-borane complex (2) as a viscous liquid. $^{11}$B NMR (CDCl$_3$): δ 53.7.

Preparation of complex of tris-(2-methylene-cyclopropyl)-borane:

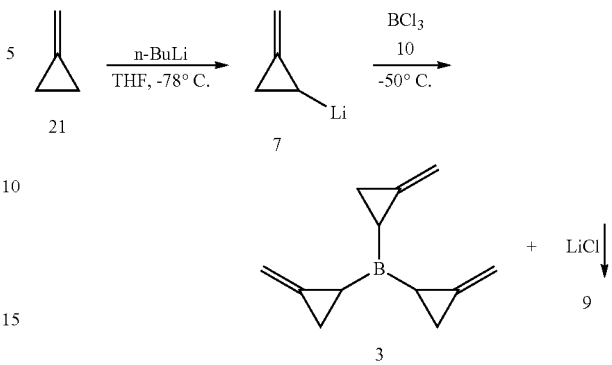

An oven-dried 100 mL schlenk flask cooled at −78° C. was charged with MCP (21) (0.99 g, 18.5 mmol) in 30 mL of anhydrous THF. 7.2 mL of 2.5 M n-BuLi in hexane (18 mmol) was added slowly and stirred at room temperature for 4 h. The mixture was cooled at −50° C. A mixture of condensed boron trichloride (0.7 g, 6 mmol) in 2 mL of hexane was added slowly to the reaction solution over 15 min. The reaction mixture was stirred at room temperature for 36 h. The solution was filtered to remove salt and concentrated in vacuo. The precipitated solid was removed by filtration. The reaction mixture was dissolved in 30 mL of pentane and passed through a pad of celite under nitrogen. The solution was concentrated in vacuo and dried under vacuum to obtain tris-(2-methylene-cyclopropyl)-borane (3) as a viscous liquid. $^{11}$B NMR in CDCl$_3$: δ 29.0.

Synthetic procedure ffor DPMB (4): An oven-dried 100 mL schlenk flask cooled at −78° C. under argon was charged with MCP (0.81 g, 15.0 mmol) in 30 mL of anhydrous THF. To the mixture, 5.6 mL of 2.5 M n-hexane (14 mmol) was added slowly and stirred at room temperature for 4 h. The mixture was cooled at −50° C. and 2.8 g (14 mmol) of diphenyl chloroborane (8) dissolved in 15 mL of toluene was added slowly over 20 min. The reaction mixture was stirred at room temperature for 36 h. The solution was filtered to remove salt and concentrated in vacuo. The product was dissolved in 5 mL anhydrous CH$_2$Cl$_2$ and filtered with syringe filter to remove the precipitated salt (9), repeated this process to get a clear solution and concentrated in vacuo to obtain 1.9 g (63% yield) of DPMB (4) complex. $^{11}$B NMR (CDCl$_3$): δ 45.6. Structure of DPMB:

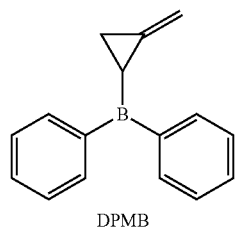 [SMILES: C=C1CC1B(c1ccccc1)c1ccccc1 ; "DPMB"]

DPMB

Synthetic procedure of Bis-biphenyl-4-yl-dimethyl-starmane (23): An oven-dried 200 mL Schlenk flask cooled under argon was charged with 2.4 g Mg turnings (100 mmol) and 40 mL of anhydrous THF. To the mixture, 16.6 g (71.2 mmol) of 4-Bromo-biphenyl dissolved in 30 mL of anhydrous THF was slowly added via a cannula. The reaction mixture was refluxed for 2 h and cooled at room temperature. The freshly prepared Grignard reagent was transferred via cannula in to a 200 mL 3-neck flask equipped with a condenser and cooled at 0° C. A solution of dichlorodimetthylsilane (5 g, 22.8 mmol) in 10 mL of dry THF was added in to the 3-neck flask via a cannula. The mixture was stirred for 30 minutes at room temperature before it was refluxed for 3 h. The reaction mixture was stirred at room temperature for 16 h. After the reaction the solution was cooled at 0° C., it was treated little by little with total 10 mL of saturated NH$_4$Cl solution and extracted with dichloromethane in a separating funnel. The organic layer was washed three times with total of 150 mL water, concentrated in vacuo to give crude product mixed with biphenyl. The crude product was mixed with 25 mL of hexane and filtered under vacuum to obtain 9.6 g (89% yield) of 23 as white powder. $^1$H-NMR (400 MHz, CDCl$_3$): δ 0.56 (3H, s). 7.33 (1H, t, J=7.5 Hz), 7.42 (2H, t, J=7.5 Hz), 7.54-7.64 (6H, m); $^{13}$C NMR (100 MHz, CDCl$_3$) δ −9.98, 126.9, 127.1, 127.3, 128.7, 136.6, 139.3, 141.1, 141.4.

Synthetic procedure of Bis-biphenyl-4-yl-chloro-borane (24); An oven dry 100 mL thick-wall flask with Teflon screw cap cooled under argon was charged with 5 g (11 mmol) of Bis-biphenyl-4-yl-dimethyl-stannane (23), 11 mL of 1M Borontrichloride solution (11 mmol) in heptane and 50 mL of anhydrous heptane in a nitrogen saturated glove box. The mixture was stirred for 30 minutes at room temperature and then heated at 110° C. for 48 h. After the reaction, the solution was cooled and subjected to vacuum filtration under nitrogen in the glove box. The solid was washed three times with a total 15 mL of dry dichloromethane to remove dichlorodimetthylsilane. The rest of dichlorodimetthylsilane was removed by sublimation technique to obtain 1.6 g of 24 (41.3% yield) as a white powder. $^{11}$B NMR (CDCl$_3$): δ 63.2; $^1$H-NMR (400 MHz, CDCl$_3$): δ 7.40 (1H, t, J=7.6 Hz), 7.48 (1H, t, J=7.6 Hz), 7.68 (1H, d, J=7.6 Hz), 7.74 (1H, d, J=7.6 Hz), 8.12 (1H, d, J=8.4 Hz); $^{13}$C NMR (100 MHz, CDCl$_3$) δ 126.5, 127.3, 128.0, 128.9, 136.4, 137.6, 140.3, 145.5.

Synthetic procedure of Bis-biphenyl-4-yl-(2-methylene-cyclopropyl)-borane, BPMB (25): An oven-dried 100 mL Schlenk flask cooled at −78° C. was charged with MCP (0.44 g, 8.2 mmol) in 15 mL of anhydrous THF. To the solution, 2.5 mL of 2.5 M n-BuLi in hexane (6.2 mmol) was added slowly and stirred at room temperature for 3 h. The mixture was cooled at −50° C. and 2 g (5.7 mmol) of Bis-biphenyl-4-yl-chloro-borane (24) dissolved in 20 mL of dry THF was added slowly over 15 min via a cannula. The reaction mixture was stirred at room temperature for 24 h. The solution was filtered to remove salt and concentrated in vacuo. The solid was dissolved in 15 mL of dichloromethane and filtered with a syringe filter to get a clear solution. The solution was concentrated in vacuo and dried under vacuum to obtain 1.6 g (76% yield) of BPMB (11) as a solid. $^{11}$B NMR (CDCl$_3$): δ 33.0. Structure for BPMB:

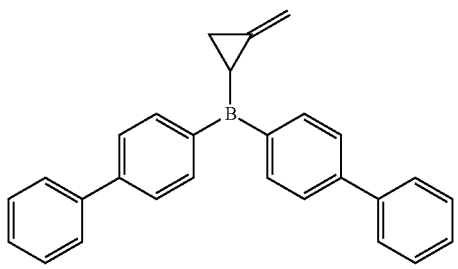

BPMB (25)

Following the same synthetic procedures of making 23, 24 and 25, we will be able to make 26, 27, 28 by replacing the starting material with 1-Bromonapthalene, 2-Bromonapthalene and 9-Bromophenanthrene respectively:

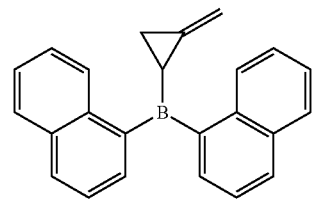 [SMILES: C=C1CC1B(c1cccc2ccccc12)c1cccc2ccccc12]

Bis-naphthyl-1-yl-(2-methylene-cyclopropyl)-borane, BNMBa (26)

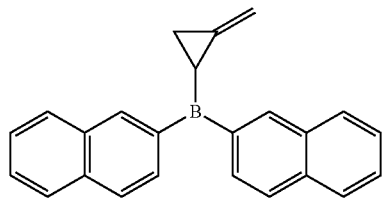 [SMILES: C=C1CC1B(c1ccc2ccccc2c1)c1ccc2ccccc2c1]

Bis-naphthyl-2-yl-(2-methylene-cyclopropyl)-borane, BNMBb (27)

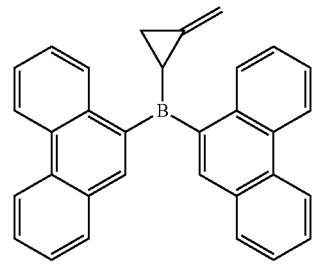 [SMILES: C=C1CC1B(c1cc2ccccc2c2ccccc12)c1cc2ccccc2c2ccccc12]

Bis-phynanthryl-9-yl-(2-methylene-cyclopropyl)-borane, BPNMB (28)

More hypothetical compound could be synthesized using similar procedures, including the following: Bis-2-methyl-naphthyl-1-yl-(2-methylene-cyclopropyl)-borane; Bis-fluorenyl-3-yl-(2-methylene-cyclopropyl)-borane; Bis-fluorenyl-9-yl-(2-methylene-cyclopropyl)-borane; Bis-diphenylmethyl-(2-methylene-cyclopropyl)-borane; Bis-anthracenyl-9-yl-(2-methylene-cyclopropyl)-borane.

Investigation of releasing 1-MCP from the boron complexes of MCP (1, 2, 3,4): Without being bound by theory, due to the moisture sensitivity of the boron complexes, the nucleophilic attack of hydroxide ion (OH—) toward the boron atom triggered the breaking of the B-C bond releasing 1-MCP as a gas.

Figure 4:
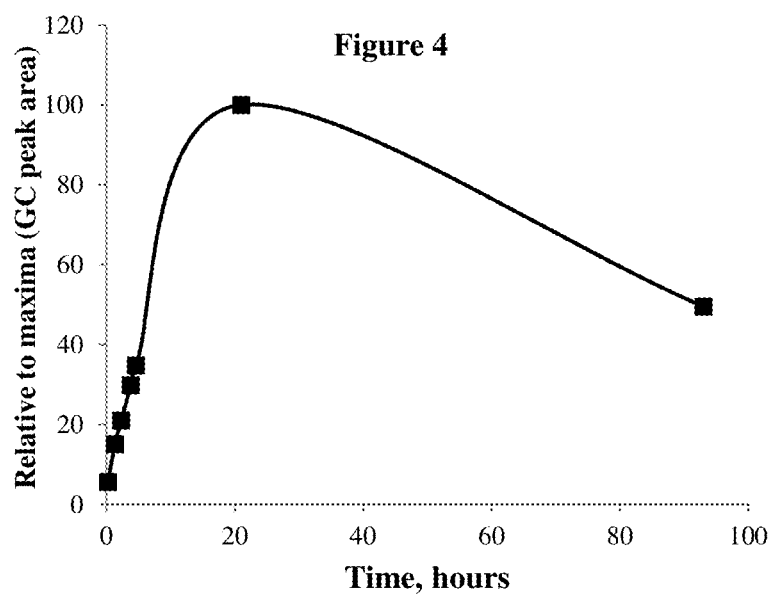
FIG. 4 shows MCP releasing curve of compound 1 as described below.

GC analysis of dicyclohexyl-(2-methylene-cyclopropyl)-borane (1): 140 mg of the complex was mixed vigorously with 0.6 mL of H$_2$O in a 1.5 mL air-tight vial. The vapor collected (8 μl) from the head space of the solution was injected in a GC with an MXT$_{R-1}$ column. The data were compared with a reference standard of 1-MCP. Surprisingly it was found that 1-MCP was released gradually with time (FIG. 4).

Figure 5:
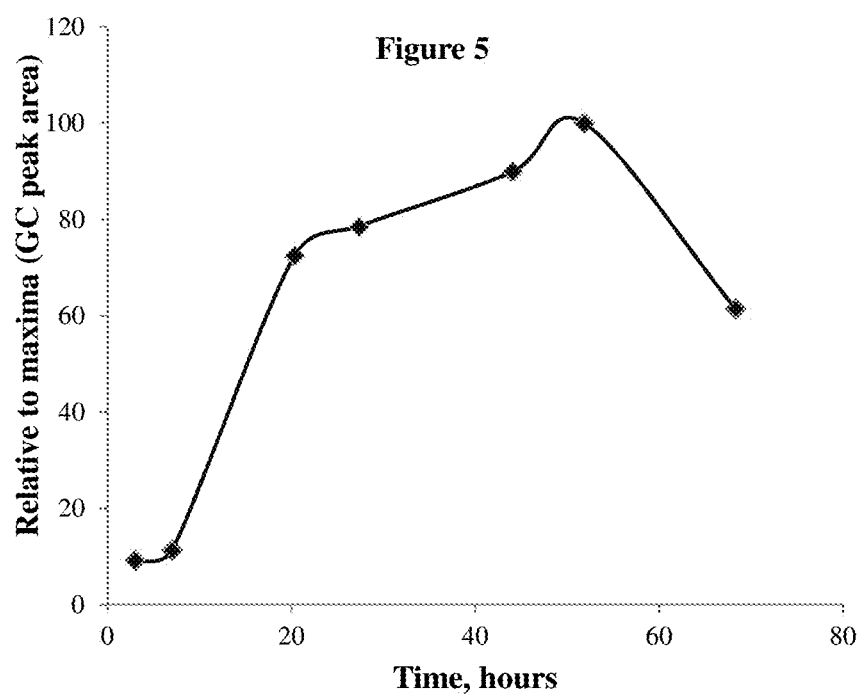
FIG. 5 shows MCP releasing curve of compound 2 as described below.

GC analysis of dihexyl-(2-methylene-cyclopropyl)-borane (2): 291 mg of the complex was mixed vigorously with 1.0 mL of $H_2O$ in a 3 mL air-tight vial. The vapor collected (100 μL) from the head space of the solution was injected in a GC with an $MXT_{R-1}$ column. The data were compared with a reference standard of 1-MCP. Surprisingly it was found that 1-MCP was released gradually with time (FIG. 5).

Figure 6:
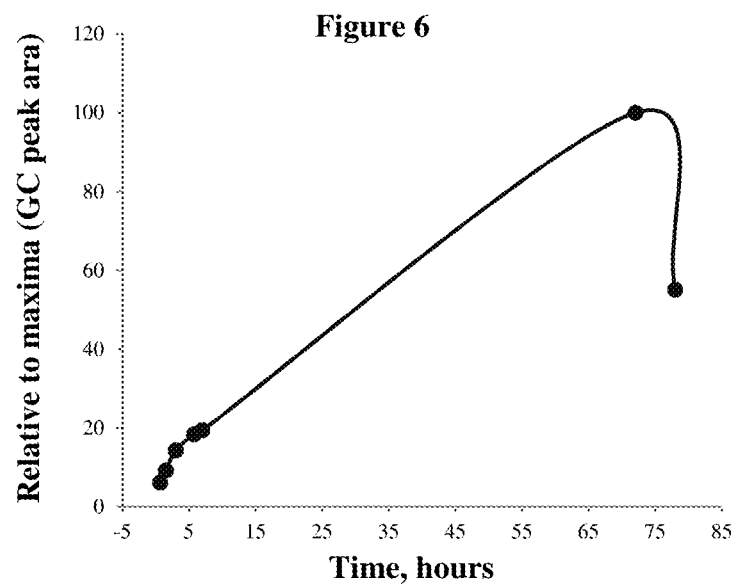
FIG. 6 shows MCP releasing curve of compound 3 as described below.

GC analysis of tris-(2-methylene-cyclopropyl)-borane (3): 94 mg of the complex was mixed vigorously with 0.4 mL of $H_2O$ in a 1.5 mL air-tight vial. The vapor collected (8 μL) from the head space of the solution was injected in a GC with an $MXT_{R-1}$ column. The data were compared with a reference standard of 1-MCP. Surprisingly it was found that 1-MCP was released gradually with time (FIG. 6).

Figure 7:
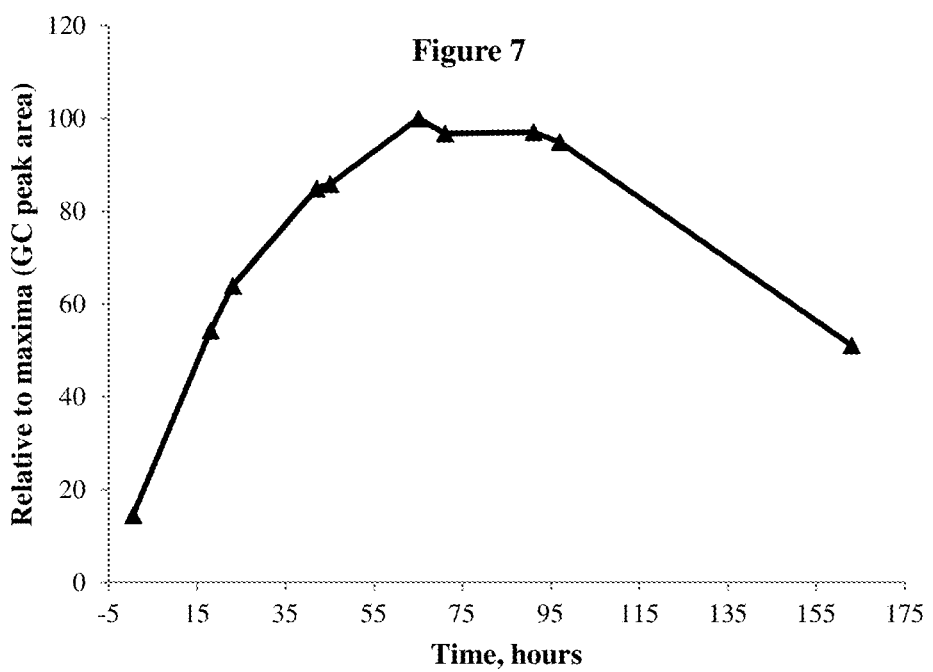
FIG. 7 shows MCP releasing curve of compound 4 as described below.

GC analysis of diphenyl-(2-methylene-cyclopropyl)-borane (4): 393 mg of the complex was mixed vigorously with 2.0 mL of $H_2O$ in a 3 mL air-tight vial. The vapor collected from the head space of the solution was injected in a Hewlett-Packard 5890 GC with capillary column (30 m×0.25 mm i.d.) coated with a 0.25 μm film of 5% phenyl methyl silicon and a flame ionization detector. The temperature of GC was programmed at 30° C. isothermal with an injection point temperature of 50° C. The detector was operated at 230° C. and sample was injected under split less condition. Helium was used as carrier gas with a 1.5 mL/min column flow. Surprisingly it was found that 1-MCP was released gradually with time (FIG. 7).

Figure 8:
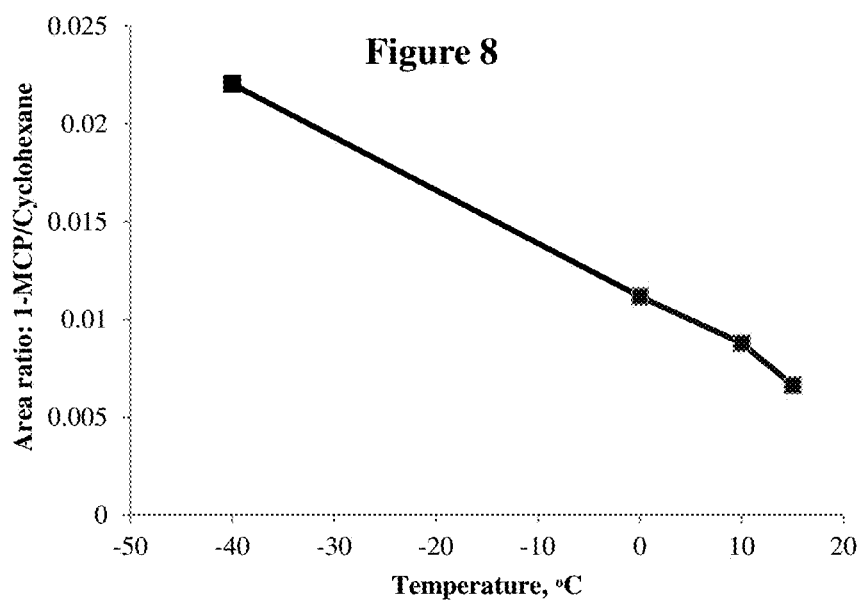
FIG. 8 shows the area ratio of 1-MCP/cyclohexane vs. temperature released from complex 1 as described below.

From FIGS. 4-7 it was evident that although all three complexes surprisingly had the capability of gradual release of 1-MCP, dicyclohexyl-(2-methylene-cyclopropyl)-borane (1) and tris-(2-methylene-cyclopropyl)-borane (3) were surprisingly more consistent in releasing 1-MCP over time than dihexyl-(2-methylene-cyclopropyl)-borane (2). However, during this analysis it was observed that some other compounds were also released. Those compounds formed due to the breakage of other B-C bonds were cyclohexane and cyclohexanol from complex 1 or hexane and hexanol from complex 2. Complex 3 also released some byproducts either by incomplete hydrolysis of the complex or Markovnikov addition of $H_2O$. These complexes will still be useful in control release of 1-MCP as all the byproducts had a much higher boiling point than 1-MCP (~12° C.). To demonstrate this, we investigated the GC experiment at different temperatures. The area ratio of released 1-MCP over cyclohexane was surprisingly increased at lower temperature (FIG. 8).

Boron complex 1 was tested on green tomatoes. Six 3.9 L air tight glass jars were taken for investigation containing five green tomatoes each. The tomatoes in three jars were treated with 1-MCP released from the reaction between Boron complex 1 and water in a 14 mL vial with continuous stirring, which was placed inside the jars. The other jars were kept in identical condition without placing any boron complex inside. The treatment was carried out for 24 hours. The concentration level of 1-MCP was determined (9 to 13 $μLL^{-1}$) after 24 hours of reaction by GC analysis using 2-methyl-1-propene as a standard. After 24 hours treatment all the tomatoes were kept in open environment and monitored for their color changes.

Figure 9:
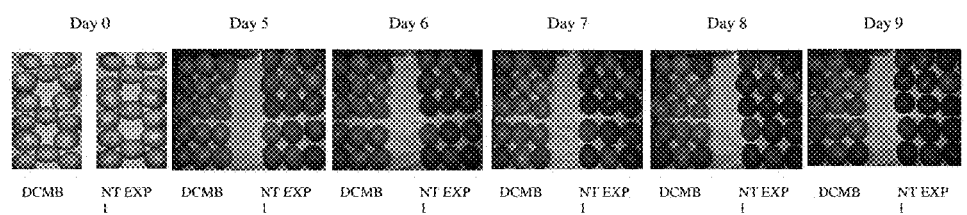
FIG. 9 shows comparison of tomatoes treated with Boron complex 1 and untreated controls as described below.

Distinctive color differences were observed after 4 days, where 1-MCP treated tomatoes surprisingly remained green but untreated tomatoes turned yellow (FIG. 9). The same progress continued until all untreated tomatoes turned red at the end of nine days although surprisingly half of the treated tomatoes were still green. This clearly showed that 1-MCP released from dicyclohexyl-(2-methylene-cyclopropyl)-borane (1) complex and water has significant impact to inhibit the ethylene activity on tomatoes even at lower concentration level. No foreign spots were observed on the surface of the treated tomatoes.

For the comparative studies between DCMB (1) and DPMB (4), experiment was performed with three 1-gal airtight jars containing eight tomatoes each which were collected from the same source but different time. One jar was used as blank containing no complex and the other two jars Were treated with equivalent amount of DCMB (1) (393 mg) and DPMB (4) (376.5 mg) complex respectively arid water (2 mL), The concentration of released 1-MCP inside the jars was calculated by GC analysis after 24 hour treatment The treated and untreated tomatoes were subjected to quality analysis under identical conditions.

Quality Analysis: Noninoculated tomatoes were treated with Boron complex 1 as described before and kept in open air for 9 days. Quality analysis (color and firmness) was performed at 22±2° C. Color was measured with a Hunter UltraScan® VIS colorimeter (Hunter Associates Lab, Reston, Va.) and firmness was evaluated with a TA-XT2i Texture Analyzer (Texture Technologies Corp., Scarsdale, N.Y.). Four measurements were taken for each tomato for color and firmness. The color of the tomatoes was measured seven times during the investigation period and firmness was determined at the end of $9^{th}$ day.

Figure 10:
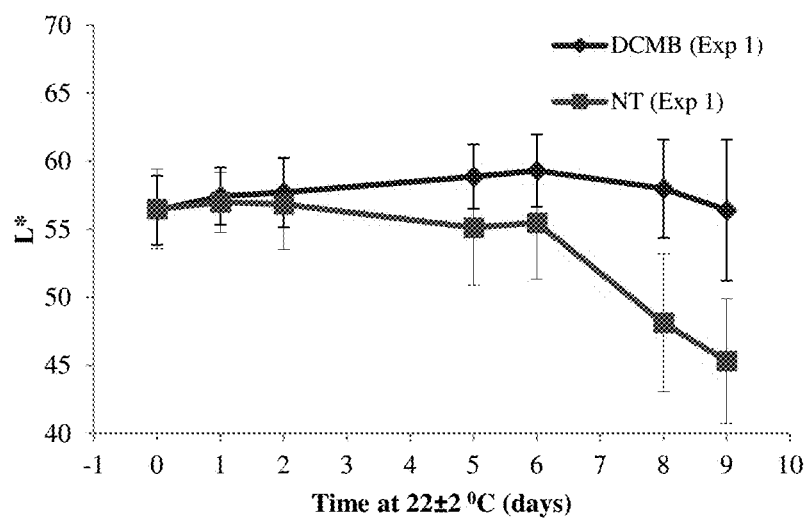
FIG. 10 shows changes in darkness (L*) of tomatoes treated with Boron complex 1 and untreated during storage at 22±2° C. as described below; vertical bars represent standard error.
Figure 11:
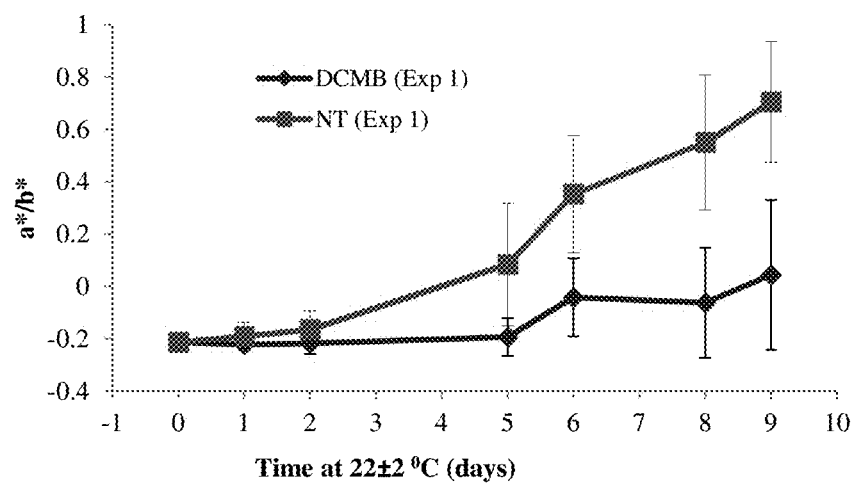
FIG. 11 shows changes in redness (a*/b*) of tomatoes treated with Boron complex 1 (T) and untreated (NT) during storage at 22±2° C. as described below; vertical bars represent standard error.

Changes in color and firmness of tomatoes during storage: L* values indicate the darkness of the tomato surface color. L* value of the tomatoes (T) which were treated with Boron Complex 1 surprisingly did not significantly change during storage, but the L* value of all the non-treated tomatoes (NT) was reduced significantly as they became dark red in color (FIG. 10). The a* and b* values represent redness and yellowness of tomatoes respectively. The higher the a* values, the redder the tomatoes were. In 9 days of storage, the a*/b* values of the treated tomatoes (T) surprisingly increased slowly but not in significant value; on the other hand, the a*/b* values for the non-treated (NT) tomatoes increased very rapidly and significantly (FIG. 11). This result suggested that the treated tomatoes (T) were surprisingly less red in comparison to the non-treated tomatoes (NT) even after 9 days of investigation.

Figure 12:
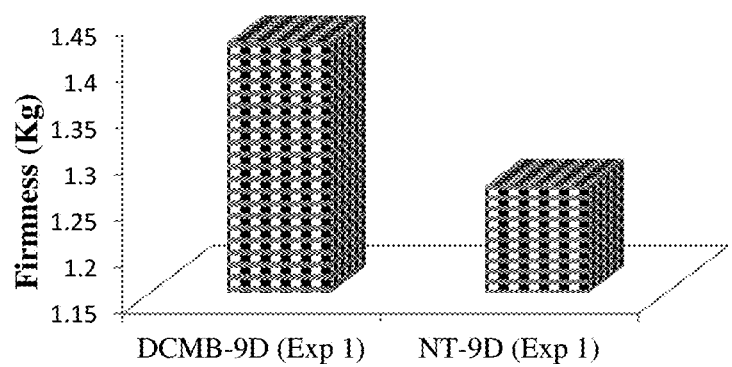
FIG. 12 shows firmness data of treated (T) and non-treated (NT) tomatoes stored at 22±2° C. as described below.

The firmness of the tomatoes which were treated with Boron complex 1 (T) was surprisingly higher than the non-treated tomatoes (NT) (FIG. 12). The values were 1.42 (±0.35) kg and 1.26 (±0.24) kg for the treated (T) and non-treated (NT) tomatoes respectively, representing a decrease of 12.24% in firmness for non-treated tomatoes (NT) during the storage time.

Figure 13:
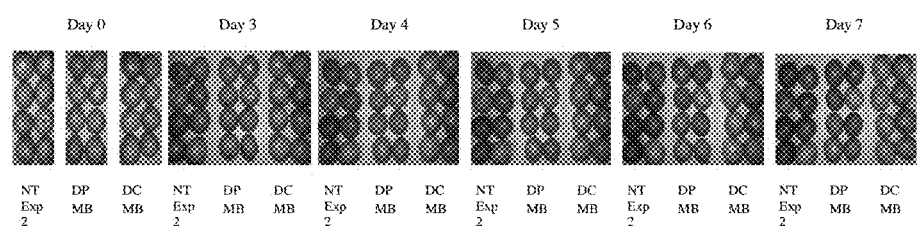
FIG. 13 shows comparison of tomatoes treated with Boron complex 1, 4 and untreated controls as described below.
Figure 14:
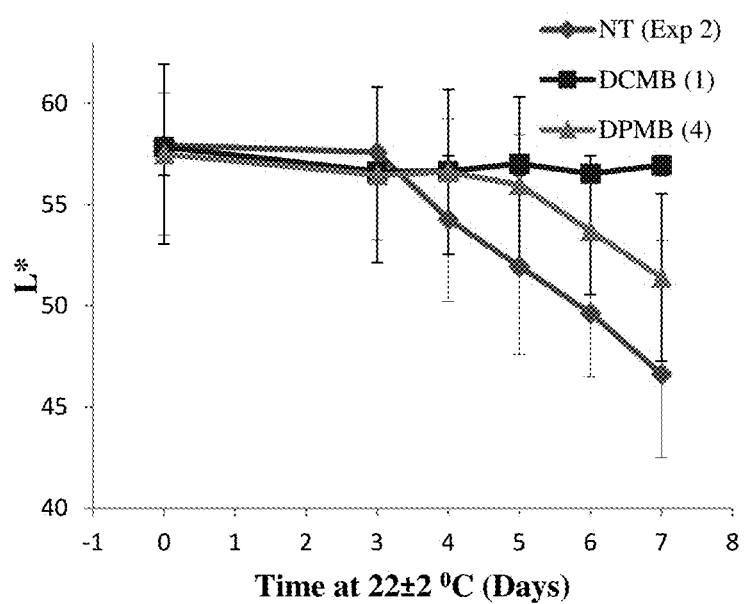
FIG. 14 shows changes in darkness (L*) of tomatoes treated with Boron complex 1, 4 and untreated during storage at 22±2° C. as described below; vertical bars represent standard error.
Figure 15:
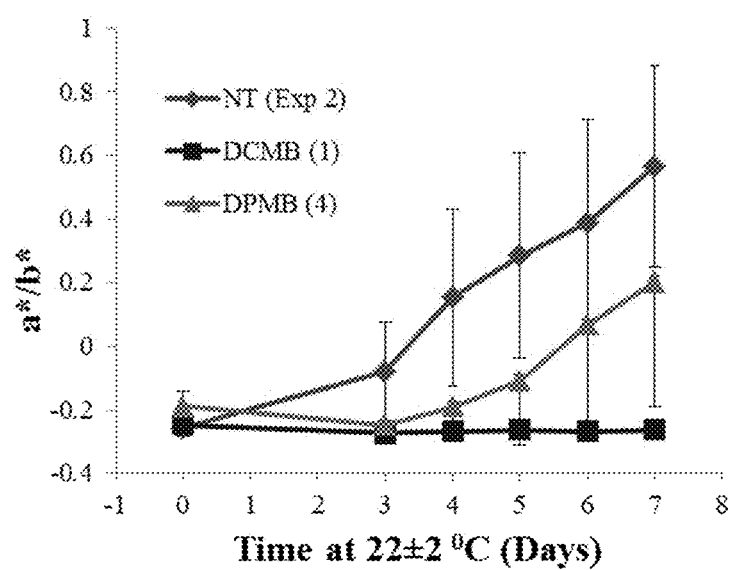
FIG. 15 shows changes in redness (a*/b*) of tomatoes treated with Boron complex 1, 4 and untreated (NT) during storage at 22±2° C. as described below; vertical bars represent standard error.
Figure 16:
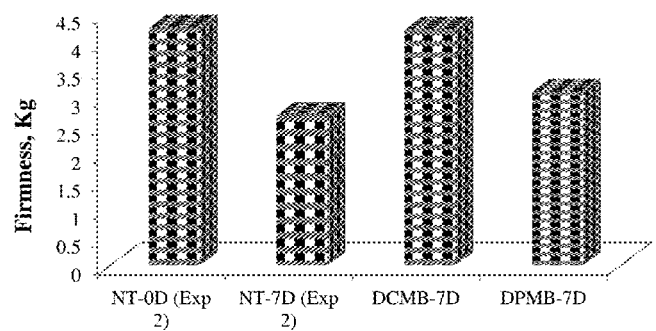
FIG. 16 shows firmness data of tomatoes treated with 1, 4 and non-treated (NT) tomatoes at day 0 and day 7 stored at 22±2° C. as described below.

Comparative Quality analysis of tomatoes treated with DCMB (1) and DPMB (4): The concentration of 1-MCP was found to be 5 μLL-1 and 1 μLL-1 for DCMB (1) and DPMB (4) respectively in 24 hours treatment even taking equivalent amount of sample. This result was surprisingly consistent with 1-MCP releasing curves (FIGS. 4 & 7), where DCMB (1) released 1-MCP near to its highest point in first 24 hours but in the case of DPMB (4) the amount of released 1-MCP was relatively low in first 24 hours. The impact of this result was visually apparent (FIG. 13). Quality analysis also surprisingly showed that L* value for DCMB (1) treated tomatoes did not significantly change during the investigation period whereas non-treated (NT, Exp. 2) tomatoes had the lowest value of L* after 7 days of storage and DPMB (4) remained in the middle (FIG. 14). Similar results were found in a*/b* value (FIG. 15). For DCMB (1) treated tomatoes this value surprisingly did not change significantly or increased very slowly, on the other hand for non-treated tomatoes the value of a*/b* started to increase rapidly and consistently from day 3 up to day 7. Significant change in color was apparent for DPMB (4) treated tomatoes from day 4 but with slower increase than the non-treated tomatoes at the end. The firmness data of the treated tomatoes was compared to that of non-treated tomatoes at Day 7 (NT-7D, Exp 2) and also at Day 0 (NT-OD, Exp 2), which were collected from the same batch. Results surprisingly showed there was no significant difference in average firmness between the DCMB (1) treated (4.20 kg) tomatoes at day 7 and non-treated tomatoes (4.24 kg) at day 0 (FIG. 16). However, a significant difference was observed between the non-treated tomatoes at day 7 (2.68 kg) and non-treated fruits at day 0. Similarly, DPMB (4) treated tomatoes showed the firmness again in the middle (3.10 kg) suggesting DCMB (1) provides better protection to keep the tomatoes fresh.

Noninoculated tomatoes were treated with Boron complex 1 as described before and kept in open air for 9 days. Quality analysis (color and firmness) was performed at 22±2° C. Color was measured with a Hunter UltraScan® VIS colorimeter (Hunter Associates Lab, Reston, Va.) and firmness was evaluated with a TA-XT2i Texture Analyzer (Texture Technologies Corp., Scarsdale, N.Y.). Four measurements were taken for each tomato for color and firmness. The color of the tomatoes was measured seven times during the investigation period and firmness was determined at the end of 9th day.

Changes in color and firmness of tomatoes during storage: $L^*$ values indicate the darkness of the tomato surface color. $L^*$ value of the tomatoes (T) which were treated with Boron Complex 1 surprisingly did not significantly change during storage, but the $L^*$ value of all the non-treated tomatoes (NT) was reduced significantly as they became dark red in color (FIG. 10). The $a^*$ and $b^*$ values represent redness and yellowness of tomatoes respectively. The higher the $a^*$ values, the redder the tomatoes were. In 9 days of storage, the $a^*/b^*$ values of the treated tomatoes (T) surprisingly increased slowly but not in significant value; on the other hand, the $a^*/b^*$ values for the non-treated (NT) tomatoes increased very rapidly and significantly (FIG. 11). This result suggested that the treated tomatoes (T) were surprisingly less red in comparison to the non-treated tomatoes (NT) even after 9 days of investigation.

The firmness of the tomatoes which were treated with Boron complex 1 (T) was surprisingly higher than the non-treated tomatoes (NT) (FIG. 12). The values were 1.42 (±0.35) kg and 1.26 (±0.24) kg for the treated (T) and non-treated (NT) tomatoes respectively, representing a decrease of 12.24% in firmness for non-treated tomatoes (NT) during the storage time.

Comparative Quality analysis of tomatoes treated with DCMB (1) and DPMB (4): The concentration of 1-MCP was found to be 5 µLL-1 and 1 µLL-1 for DCMB (1) and DPMB (4) respectively in 24 hours treatment even taking equivalent amount of sample. This result was surprisingly consistent with 1-MCP releasing curves (FIG. 4 & 7), where DCMB (1) released 1-MCP near to its highest point in first 24 hours but in the case of DPMB (4) the amount of released 1-MCP was relatively low in first 24 hours. The impact of this result was visually apparent (FIG. 13). Quality analysis also surprisingly showed that $L^*$ value for DCMB (1) treated tomatoes did not significantly change during the investigation period whereas non-treated (NT, Exp. 2) tomatoes had the lowest value of $L^*$ after 7 days of storage and DPMB (4) remained in the middle (FIG. 14). Similar results were found in $a^*/b^*$ value (FIG. 15). For DCMB (1) treated tomatoes this value surprisingly did not change significantly or increased very slowly, on the other hand for non-treated tomatoes the value of $a^*/b^*$ started to increased rapidly and consistently from day 3 up to day 7. Significant Change in color was apparent for DPMB (4) treated tomatoes from day 4 but with slower increase than the non-treated tomatoes at the end. The firmness data of the treated tomatoes was compared to that of non-treated tomatoes at Day 7 (NT-7D, Exp 2) and also at Day 0 (NT-OD, Exp 2), which were collected from the same batch. Results surprisingly showed there was no significant difference in average firmness between the DCMB (1) treated (4.20 kg) tomatoes at day 7 and non-treated tomatoes (4.24 kg) at day 0 (FIG. 16). However, a significant difference was observed between the non-treated tomatoes at day 7 (2.68 kg) and non-treated fruits at day 0. Similarly, DPMB (4) treated tomatoes showed the firmness again in the middle (3.10 kg) suggesting DCMB (1) provides better protection to keep the tomatoes fresh.

Conclusion: We have shown that the boron complexes (1, 2, 3, 4) surprisingly had the capability of releasing 1-MCP in a control way under ambient conditions. It will surely solve not only the handling problem of 1-MCP but also allow for its gradual release. By releasing 1-MCP gradually we will have the benefit of exposing fruits and vegetables to 1-MCP for a longer time even in open place. This will save costs associated with refrigerated storage as well as open the new fields of application where controlled release of 1-MCP is the only option0;(e.g., in direct use in crop fields to protect crops from drought).

All of the references cited herein, including U.S. Patents, are incorporated by reference in their entirety. Also incorporated by reference in their entirety are the following U.S. Pat. Nos.: 8,680,121; 8,658,570; 8,629,083; 8,603,524; 8,461,086; 8,414,989; 8,357,747; 8,329,954; 8,314,051; 8,256,190; 8,163,244; 6,897,185; 6,684,605; 6,460,316; 6,357,207; 6,017,849; 5,518,988.

Thus, in view of the above, there is described (in part) the following:

A compound having one of the following formulae:

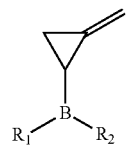

wherein $R^1$ and $R^2$ are alkyl or aryl and $R^1$ and $R^2$ may be the same or different,

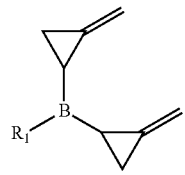

wherein $R^1$ is alkyl or aryl, or

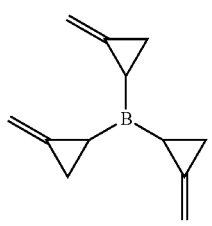

wherein alkyl is a linear or branched, saturated or unsaturated alkyl having C1-20 and wherein aryl is an aromatic ring having C6-15.

A composition comprising (or consisting essentially of or consisting of) the above compound and optionally a carrier. The above composition containing a carrier.

A method of inhibiting an ethylene response in a plant, comprising (or consisting essentially of or consisting of) applying to said plant an effective ethylene response-inhibiting amount of the above compound and optionally a carrier. The above method, wherein said plant is a crop in the field. The above method, wherein said applying step is carried out by contacting said plant to a gas of said compound or spraying said plant with a solution comprising (or consisting essentially of or consisting of) said compound or contacting said plant to a solid comprising (or consisting essentially of or consisting of) said compound.

A method of inhibiting abscission in a plant, comprising (or consisting essentially of or consisting of) applying to the plant an effective abscission-inhibiting amount of the above compound and optionally a carrier. The above method, wherein said applying step is carried out by contacting said plant to a gas of said compound or spraying said plant with a solution comprising (or consisting essentially of or consisting of) said compound or contacting said plant to a solid comprising (or consisting essentially of or consisting of) said compound.

A method of prolonging the life of a cut flower, comprising (or consisting essentially of or consisting of) applying to the cut flower an effective life-prolonging amount of the above compound and optionally a carrier. The above method, wherein said applying step is carried out by contacting said plant to a gas of said compound or spraying said plant with a solution comprising (or consisting essentially of or consisting of) said compound or contacting said plant to a solid comprising (or consisting essentially of or consisting of) said compound.

A method of delivering a compound to a plant to inhibit an ethylene response in the plant, the method comprising (or consisting essentially of or consisting of) the step of contacting the above compound and optionally a carrier, and thereby liberating MCP from the compound so that it can contact the plant.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. A compound having one of the following formulae:

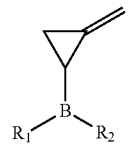

wherein $R^1$ and $R^2$ are alkyl or aryl and $R^1$ and $R^2$ may be the same or different,

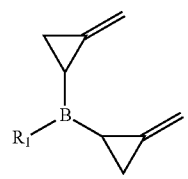

wherein $R^1$ is alkyl or aryl, or

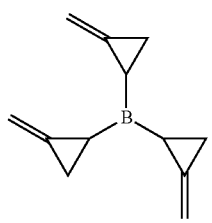

wherein said alkyl is a linear or branched, saturated or unsaturated alkyl having C6-20 and wherein said aryl is an aromatic ring having C6-15.

2. A composition comprising a compound according to claim 1 and optionally a carrier.

3. A method of inhibiting an ethylene response in a plant, comprising applying to said plant an effective ethylene response-inhibiting amount of the compound according to claim 1 and optionally with a carrier.

4. The method according to claim 3, wherein said plant is a crop in the field.

5. The method according to claim 3, wherein said applying is carried out by contacting said plant with a gas of said compound or spraying said plant with a solution comprising said compound or contacting said plant with a solid comprising said compound.

6. A method of inhibiting abscission in a plant, comprising applying to the plant an effective abscission-inhibiting amount of a compound according to claim 1 and optionally with a carrier.

7. The method according to claim 6, wherein said applying is carried out by contacting said plant with a gas of said compound or spraying said plant with a solution comprising said compound or contacting said plant with a solid comprising said compound.

8. A method of prolonging the life of a cut flower, comprising applying to the cut flower an effective life-prolonging amount of the compound according to claim 1 and optionally with a carrier.

9. The method according to claim 8, wherein said applying is carried out by contacting said cut flower with a gas of said compound or spraying said cut flower with a solution comprising said compound or contacting said cut flower with a solid comprising said compound.
10. The compound according to claim 1, wherein said compound is
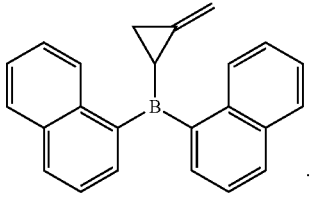 [SMILES: C=C1CC1B(c1cccc2ccccc12)c1cccc2ccccc12]
11. The compound according to claim 1, wherein said compound is
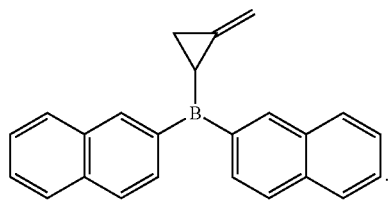 [SMILES: C=C1CC1B(c1ccc2ccccc2c1)c1ccc2ccccc2c1]
* * * * *